United States Patent
Huang et al.

(10) Patent No.: US 10,368,832 B2
(45) Date of Patent: Aug. 6, 2019

(54) LUNG TISSUE IDENTIFICATION IN ANATOMICALLY INTELLIGENT ECHOCARDIOGRAPHY

(71) Applicant: KONINKLIJKE PHILIPS N.V., Eindhoven (NL)

(72) Inventors: Sheng-Wen Huang, Cambridge, MA (US); Emil George Radulescu, Ossining, NY (US); Ramon Quido Erkamp, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 576 days.

(21) Appl. No.: 14/900,788

(22) PCT Filed: Jun. 18, 2014

(86) PCT No.: PCT/IB2014/062321
§ 371 (c)(1),
(2) Date: Dec. 22, 2015

(87) PCT Pub. No.: WO2014/207611
PCT Pub. Date: Dec. 31, 2014

(65) Prior Publication Data
US 2016/0151040 A1 Jun. 2, 2016

Related U.S. Application Data
(60) Provisional application No. 61/840,681, filed on Jun. 28, 2013.

(51) Int. Cl.
*A61B 8/00* (2006.01)
*A61B 8/08* (2006.01)
(Continued)

(52) U.S. Cl.
CPC ............ *A61B 8/0858* (2013.01); *A61B 8/085* (2013.01); *A61B 8/14* (2013.01); *A61B 8/463* (2013.01);
(Continued)

(58) Field of Classification Search
CPC ....... A61B 8/0858; A61B 8/5223; A61B 8/14; A61B 8/463; A61B 8/5215; A61B 8/48;
(Continued)

(56) References Cited

U.S. PATENT DOCUMENTS 4,534,220 A * 8/1985 Klepper ............. G01N 27/9046
73/599
6,905,467 B2 6/2005 Bradley
(Continued)

FOREIGN PATENT DOCUMENTS

| EP | 0150997 A2 | 8/1985 |
| WO | 2007025218 A2 | 3/2007 |
| WO | 2014097090 A1 | 6/2014 |

OTHER PUBLICATIONS

Averkiou, Michalakis A. et al "Nonlinear Distortion of SHort Pulses Radiated by Plane and Focused Circular Pistons", Journal Acoustic Society Am. vol. 102, No. 5, Nov. 1997.
(Continued)

*Primary Examiner* — Joel Lamprecht
(74) *Attorney, Agent, or Firm* — Sherry Womack Austin

(57) ABSTRACT

Issuance of ultrasound pulses to a volume and receiving echo data is followed by estimating, based on the received data, center frequency subvolume-by-subvolume. Distinguishing between heart and lung tissue occurs based on a result of the estimating, and may include automatically identifying a spatial boundary (332) between the heart and lung tissue (324, 328), or a user display of center frequencies that allows for visual distinguishing. The issuance can
(Continued)

include issuing, ray line by ray line, pair-wise identical, and/or pair-wise mutually inverted, ultrasound pulses. Center frequency calculations may be made for incremental sampling locations of respective imaging depth along each of the A-lines generated from echo data of the rays. The distinguishing might entail averaging center frequencies for locations along an A-line, and applying a central frequency threshold to the average. The leftmost of the qualifying A-lines, i.e., that meet the threshold, may determine the spatial boundary in the current imaging plane.

23 Claims, 8 Drawing Sheets

(51) Int. Cl.
    *G01S 7/52* (2006.01)
    *A61B 8/14* (2006.01)
    *G01S 15/89* (2006.01)

(52) U.S. Cl.
    CPC .............. *A61B 8/48* (2013.01); *A61B 8/5215* (2013.01); *A61B 8/5223* (2013.01); *G01S 7/52036* (2013.01); *G01S 7/52071* (2013.01); *G01S 7/52038* (2013.01); *G01S 15/8925* (2013.01)

(58) Field of Classification Search
    CPC . A61B 8/085; G01S 7/52071; G01S 7/52036; G01S 15/8925; G01S 7/52038
    See application file for complete search history.

(56) References Cited

U.S. PATENT DOCUMENTS

2008/0139934 A1* 6/2008 McMorrow .............. A61B 8/08
                                                                      600/438
2011/0009746 A1    1/2011 Tran

OTHER PUBLICATIONS

Averkiou et al "Self-demodulation of amplitude- and frequency-modulated pulses in a thermoviscous fluid" The Journal of Acoustical Society of America, 94, p. 2876-2883 (1993).

* cited by examiner

LUNG TISSUE IDENTIFICATION IN ANATOMICALLY INTELLIGENT ECHOCARDIOGRAPHY

CROSS-REFERENCE TO PRIOR APPLICATIONS

This application is the U.S. National Phase application under 35 U.S.C. § 371 of International Application No. PCT/IB2014/062321, filed on Jun. 18, 2014, which claims the benefit of U.S. Provisional Patent Application No. 61/840,681, filed on Jun. 28, 2013. These applications are hereby incorporated by reference herein.

FIELD OF THE INVENTION

The present invention relates to using ultrasound to distinguish between heart and lung tissue and, more particularly, to distinguishing based on center frequency estimation.

BACKGROUND OF THE INVENTION

Heart failure is a major disease with five million patients in the United States alone and tens of millions worldwide. The individuals at risk of heart failure are estimated at 60 million in the United States only; one million are hospitalized, the rest being in the care of heart failure clinics. Basic information about the heart is needed in the heart failure clinics or general practitioners' offices for patient management. This information includes images as well as quantification data, such as ejection fraction, computed from the image once the image is acquired. Ultrasound is a reliable and cost-effective imaging modality for soft tissue such as the heart.

Acquisition of an ultrasound image requires a skilled sonographer. One parameter the sonographer, or other clinician trained in sonography, optimizes is the field of view. The apical four chamber view is a standard one for routine cardiac checkups. The clinician places the head of the ultrasound probe, or "transducer probe", on the patient. An effective site on the patient's skin for placement of the probe for various views is part of the clinician's training, and the site can vary from patient to patient. For the apical four chamber view the probe is placed over the apex of the heart. The probe also needs to be manually tilted, typically in different directions until the organ is captured for imaging. This is all done interactively, with the clinician viewing the image, which is usually a sonogram, on-screen. Interpreting a sonogram is a skill that must be developed, e.g., through training and practice. The clinician's experience tells him or her, in an ongoing iterative process, how to shift and tilt the probe to achieve an effective acoustic window.

Echocardiography is challenging as the heart is surrounded by ribs and lung tissue. Ultrasound can hardly penetrate calcified ribs (typically encountered in the apical view) and lung tissue because of severe acoustic impedance mismatch between them and other soft tissues. In addition, ultrasound absorption in ribs is quite high compared to tissue. Conventionally, optimization of ultrasound image quality is done solely by the user based on real-time-displayed grayscale ultrasound images on the screen. Though experienced users are usually capable of recognizing image degradation and improving image quality accordingly by moving the probe to a better position, less experienced users might acquire compromised images because of inferior hand-eye coordination and less awareness of artifacts. Successful ultrasound scanning strongly relies on training and experience of the user.

When imaging from the apical view of the heart, a standard view, the ultrasound probe has to be placed in the right intercostal space based on the user's expertise to avoid blockage due to calcified ribs. An experienced user also makes sure lung tissue does not get into the way.

SUMMARY OF THE INVENTION

What is proposed herein below is directed to addressing one or more of the above concerns.

Commonly-assigned patent application entitled "Anatomically Intelligent Echocardiography for Point-of-Care" to Radulescu et al. (hereinafter "the Radulescu application"), the entire disclosure of which is incorporated herein by reference, relates to an ultrasound system that provides dynamic and interactive guidance to the clinician navigating an imaging probe to achieve a standard view of the heart. Part of the guidance entails lung tissue identification. The dynamic and interactive nature of the procedure is seen from FIGS. 2A and 2B in the Radulescu application.

Initially, as set forth in the Radulescu application, the system instructs the user how to place the probe intercostally. Based on the continuously acquired imaging within the field of view of the probe, the system provides feedback in the form of instructions, diagrams, audible cues, etc.

The lung identification algorithm employed by the system is designed to identify a border between heart tissue, and (partially) blocking lung tissue, in the current image. The identification serves as a cue for where the probe can be moved to get nearer to the target view. The Radulescu application also discusses automatic user guidance in navigating around image blockage caused by the patient's ribs, but the current focus in the instant patent application is image blockage due to lung tissue. A fuller discussion of the lung identification algorithm is provided herein below.

To attain good image quality for an inexperienced user, an anatomically intelligent echocardiograph system should be aware of the presence of lung tissue.

In accordance with an aspect of the present invention, ultrasound pulses are issued to a volume and echo data is received. Based on the received data, center frequency is estimated sub-volume by sub-volume so as to allow heart tissue to be distinguished from lung tissue.

According to a sub-aspect, the distinguishing entails automatic identifying of a spatial boundary between the heart and lung tissue.

In a further, particular sub-aspect, an apparatus, in accordance with the invention, can include a matrix probe, with the above-noted boundary having a three-dimensional path. The apparatus further comprises a display. The apparatus is configured for displaying, via the display, the path multi-dimensionally for a given position of the probe.

In a yet further, specific sub-aspect, the displaying uses a representation that shows how lateral and elevational components of the path jointly vary along the path.

In a different but related sub-aspect, an apparatus for identifying a spatial boundary includes a display, and an ultrasound imaging probe for the issuing and the receiving, and presents, via the display, the identified boundary for user guidance in moving the probe to achieve a target view.

As a further sub-aspect, the user guidance may be dynamic and interactive.

As a sub-aspect related to the automatic identifying, the distinguishing includes selecting from among A-lines based on the result of the estimating.

In a further sub-aspect, the selecting involves applying a center-frequency threshold location-by-location along the A-lines.

In a complementary sub-aspect, the distinguishing includes qualifying candidate A-lines for the selecting, the selected A-line defining a spatial boundary between the heart and lung tissue.

In a specific sub-aspect of this, the qualifying of a candidate A-line relies on center frequency data of the candidate A-line to the exclusion of center frequency data of the other candidate A-lines.

In a different sub-aspect related to the automatic identifying, the distinguishing involves averaging center frequencies for locations along an A-line, and applying a central frequency threshold to the average.

In a further sub-aspect of this, the averaging, and respectively said applying, are iteratively performed in correspondence with different positions along the A-line.

In what is also a sub-aspect, the issuing entails issuing, ray line by ray line, pair-wise identical, and/or pair-wise mutually inverted, ultrasound pulses.

As a sub-aspect in the case of issuing pair-wise identical pulses, a difference between an echo of one of the pair and an echo of the other of the pair is computed.

In an alternative of jointly implemented sub-aspect in the case of inverted pulses, ultrasound pulse inversion is realized by which an inverted copy of a just preceding pulse is issued and an echo of the copy is summed with an echo of the just preceding pulse.

In an associated sub-aspect, the estimating is performed location-by-location along an A-line.

In still another sub-aspect, data derived from the receiving is subjected to low pass filtering.

Relatedly, the data derived from the receiving may also be subjected to high pass filtering.

In a sub-aspect, the low pass filtered data is combined with the high pass filtered data, for the estimating.

In a further sub-aspect, the combining entails assigning a first weight to the low pass filtered data, assigning a second weight to the high pass filtered data, and computing a weighted average that uses the weights.

As a supplementary aspect, the receiving involves receiving pulse inversion samples, with the estimating including the computing of a difference between, and a sum of, a pair of the samples. Low pass filtering is performed on the difference, and the high pass filtering is performed on the sum.

In a specific sub-aspect, the deriving involves computing: a) in the case of pulse inversion, a difference between an echo from a pulse and an echo from an inversion of the pulse, to yield said data to be subjected to the low pass filtering; and b) in the case of pulse subtraction, a sum of respective echoes of the pulse and a pulse identical to the pulse, to yield said data to be subjected to the low pass filtering.

Details of the novel, real-time, heart/lung distinguishing, ultrasound clinician guidance technology are set forth further below, with the aid of the following drawings, which are not drawn to scale.

DETAILED DESCRIPTION OF EMBODIMENTS

Figure 1:
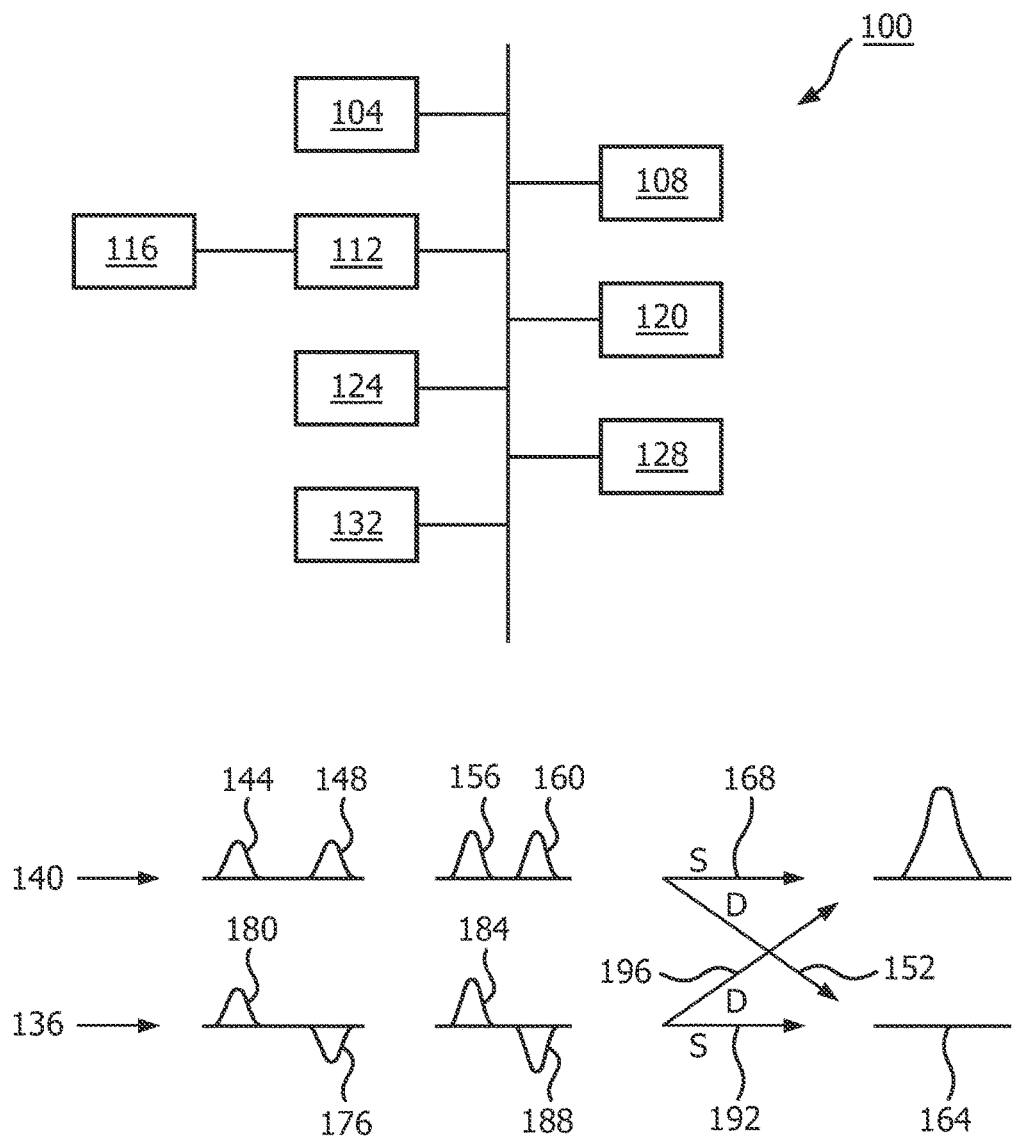
FIG. 1 is a schematic diagram of an ultrasound technician interactive guidance apparatus, with a conceptual annotation, in accordance with the present invention.

FIG. 1 depicts, by way of illustrative and non-limitative example, an ultrasound technician interactive guidance apparatus 100, with a conceptual annotation on pulsing protocols. The apparatus 100 is implementable as the device shown in FIG. 1 of the Radulescu application, including all of the circuitry mentioned, and the features shown and described for the imaging probe. Thus, the apparatus 100 may be portable as the device in FIG. 1 of the Radulescu application or a stationary device, as mentioned in the Radulescu application. Included in the apparatus 100 are a control module 104, a memory 108, an ultrasound interface module 112, the above-mentioned imaging probe 116, a center frequency determination module 120, a tissue discrimination module 124, a display 128 and user controls 132.

In an exemplary embodiment, the center frequency determination module 120 determines central frequencies for the receive beams or "A-lines" used in forming the ultrasound image. Central frequencies are computed at each incremental imaging depth along the A-line.

The tissue discrimination module 124 finds, in a fan-shaped imaging plane, a sectoring straight boundary line for distinguishing between heart and lung tissue.

In one embodiment, superimposed to the ultrasound image of a current imaging plane is a graphic of the boundary line and an arrow pointing in the direction of lung tissue. The graphics may be colored, with the boundary line red and the arrow green, for example. Likewise for a given positioning of the probe 116, the three-dimensional nature of the path of the boundary is displayable multi-dimensionally on-screen in the case of a matrix probe with electronic steering, e.g., to show variance along the path in the lateral and elevational directions. Therefore, instead of straight line overlay, a two-dimensional line is displayable on the display 128. In particular, the display 128 can depict what is visibly clearly a piece-wise end-to-end connected assemblage of line segments of alternating directionality, i.e., horizontal or vertical, giving the appearance of a curved line. Or, the presentation can be smoothed to more realistically resemble a curved line.

Annotated to the ultrasound interface module 112 in FIG. 1 is a conceptual representation of pulse inversion (PI) 136 and pulse subtraction (PS) 140, either of which or both of which can be used in the technology proposed herein. In a PS protocol, a first PS pulse 144 is followed by an identical second PS pulse 148. Here, for simplicity of demonstration, merely the positive half of a single pulse cycle is shown. The difference 152 between the corresponding echoes 156, 160 is a null signal 164 due to cancellation in the hypothetical case of purely linear propagation and a purely linear response by stationary scatterers. Summation 168, given the same circumstances, yields output with a magnitude double that of the two echoes added. In a PI protocol, the second PI pulse is an identical but inverted copy 176 of the first pulse 180. The echoes 184, 188 under the linear conditions mentioned above are identical but inverted copies of each other. Summation 192 yields the null signal 164; whereas, the difference 196 yields a signal of double the magnitude. Lung and heart tissue look more different in PI or PS imaging than in conventional imaging. The use of these two pulsing protocols in the lung tissue discrimination context is discussed in more detail further below.

Figure 2:
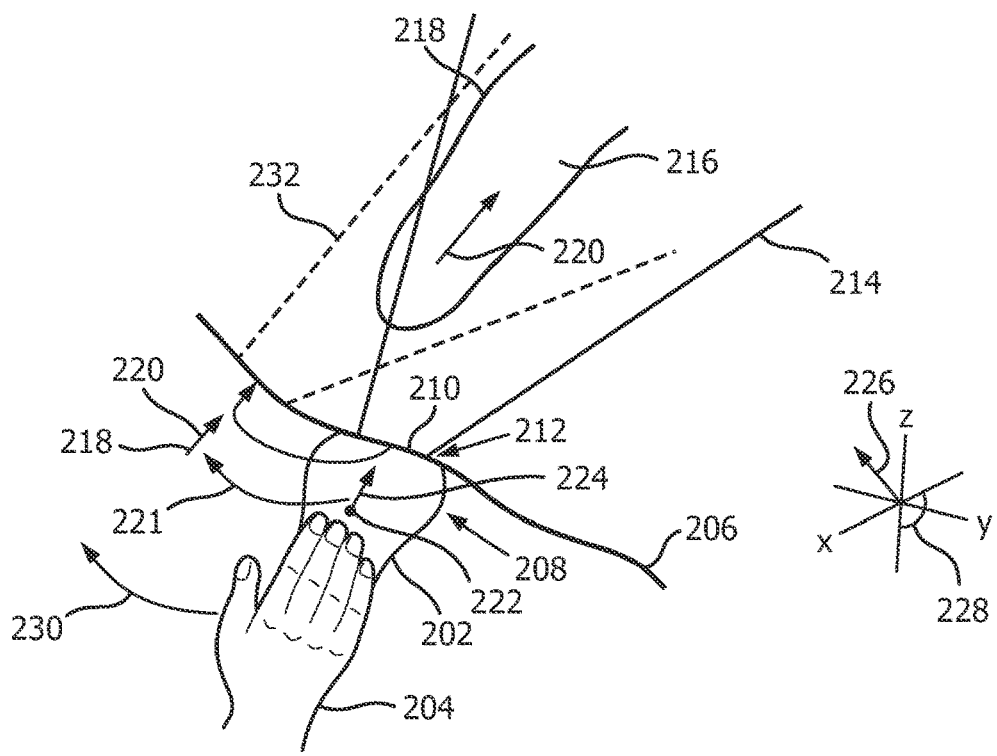
FIG. 2 is a conceptual diagram of how the apparatus is able to guide, in real time, the placement of the acoustic window.

FIG. 2 depicts, conceptually, how the apparatus 100 is able to guide, in real time, placement of a matrix probe 202. The matrix probe 202 is held by the clinician's hand 204 against the skin 206 of a patient. More specifically, the probe 202 has a head 208 which has a face 210 for placement against the skin 206, separated from the skin only by the acoustic coupling medium such as a specialized gel. Within the head 208 and along the face 210 is a matrix array 212. Extending from the matrix array 212 is a field of view 214. The heart 216 of the patient is partially, here mostly, within the field of view 214, and is being imaged via the probe 202. Since part of the heart 216 is detected with a sufficient level of confidence, the clinician has been instructed to pause and has done so promptly. As a result of image segmentation into segments 218, the apparatus 100 determines, via the model, an orientation 220 that would provide an optimal, or targeted, view of the heart 216 if the probe 202, or some part of the probe such as the matrix array 212, were to assume that orientation from an appropriate location 218. The model also provides the location 218. For simplicity of explanation, a curved arrow 221 in FIG. 2 starts at a location 222 and orientation 224 of the probe 202. It ends at the model-provided location 218 and model-provided orientation 220 that are derived from the image segmentation. The curved arrow 221 represents comparison of the field of view 214 with the model-provided location and orientation 218, 220. The comparison involves a coordinate system transformation that would bring the model-provided location and orientation 218, 220 into coincidence with the current location 222 and current orientation 224 of the probe 202. The transformation has a translational component 226 and a rotational component 228. Visual clinician-guidance feedback in the procedure is selected based on magnitudes of the components 226, 228. Another curved arrow 230 in FIG. 2 shows the clinician's hand 204 maneuvering the probe 202, based on clinician-guidance feedback, so as to achieve a field of view 232 that affords an apical view in the imaging plane of the desired orientation 220

Advantageously, the user is interactively and dynamically guided throughout a procedure for achieving an apical view of the heart.

Figure 3:
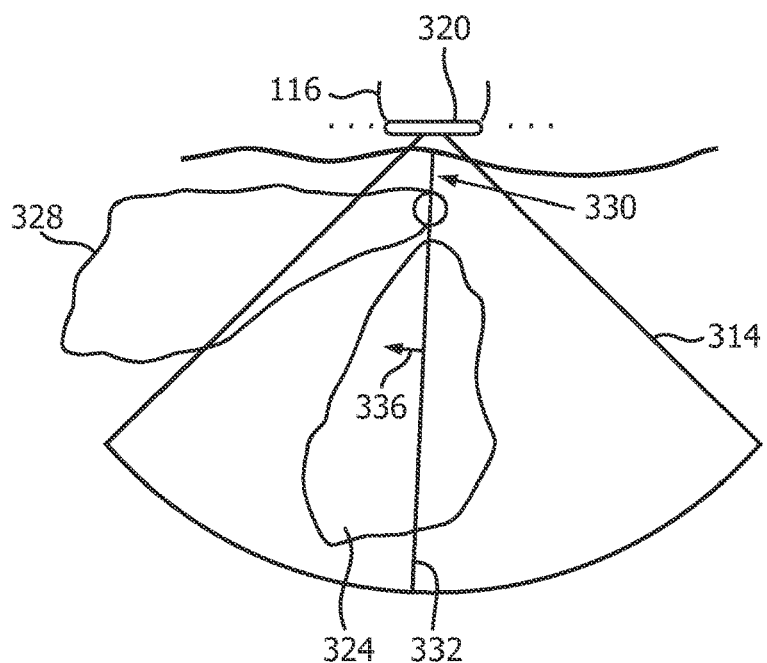
FIG. 3 is a diagram showing an example of a scheme for imaging-blockage avoidance that uses on-screen guidance images of segments disposed with respect to a field of view of an ultrasonic probe, in accordance with the present invention.

FIG. 3 shows an exemplary scheme for imaging-blockage avoidance that uses, as part of the visual feedback, on-screen guidance images of bodily organs disposed with respect to a field of view of an ultrasonic probe. The sonogram shown is an image slice that runs along the width of a patient, rather than from head to toe or from toe to head.

The matrix array 320 of the probe 116 has a current field of view 314 that includes a heart 324 and part of a lung 328. Blockage by the lung 328 exists up until an edge 330 of the lung. The algorithm calculates a blockage boundary line 332 that corresponds to the boundary between good ultrasound beams and ones that are bad due to blockage by the lung 328. An arrow 336 points to the side of the line 332 on which lung tissue is causing the blockage.

The center frequency of radiofrequency (RF) data acquired in pulse inversion (PI) modes is used as the parameter to distinguish lung tissue from heart tissue. An alternative is pulse subtraction of echoes of identical pulses, rather than the summing of respective echoes of a pulse and its inverse as in PI. The following discussion will assume PI. Although, an advantage to pulse subtraction (PS) is that mismatch between the generated positive and negative pulses is avoided.

Figure 4A:
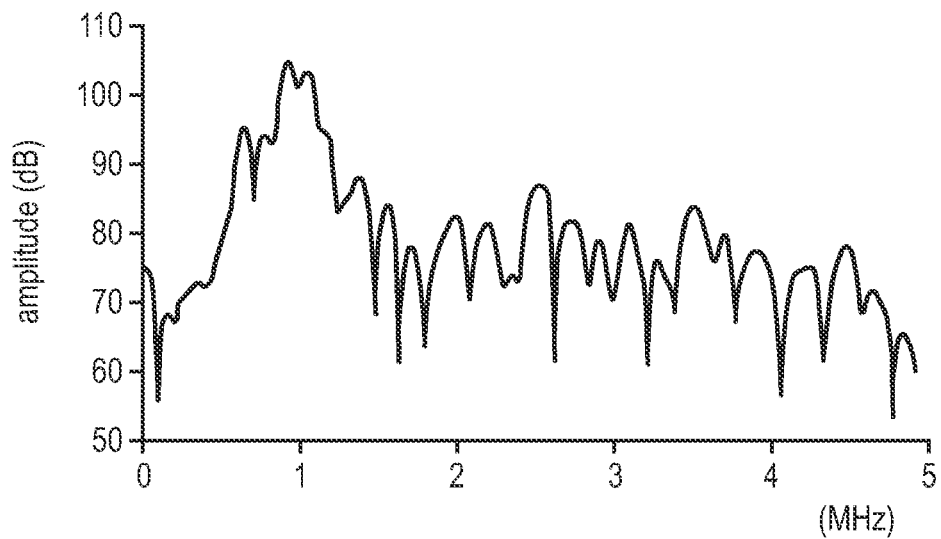
FIGS. 4A, 4B, 4C and 4D are, respectively, exemplary graphs of radiofrequency data used to distinguish lung tissue from heart tissue, an algorithm used in the distinguishing, and an exemplary center-frequency map display usable in the distinguishing, in accordance with the present invention.
Figure 4B:
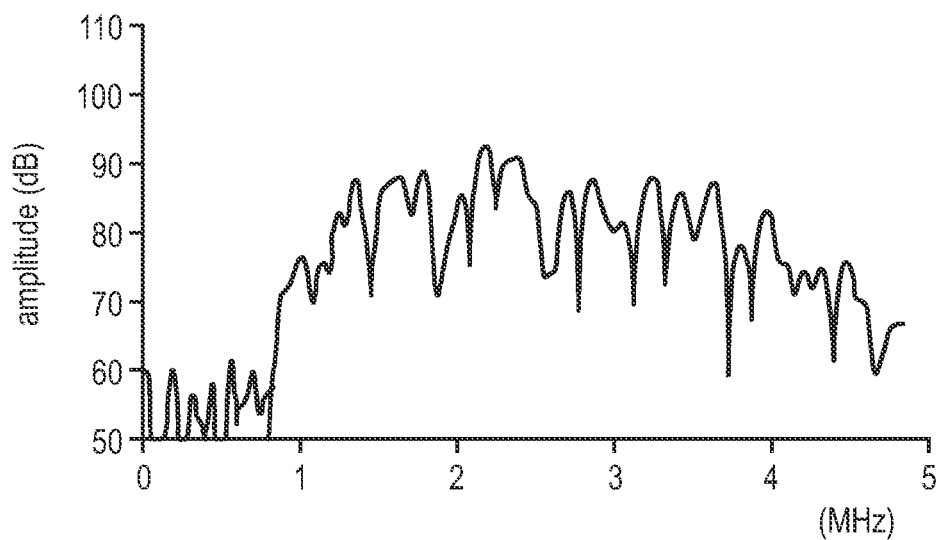

Sample radiofrequency data with a transmit center frequency of 2.1 MHz is shown in FIGS. 4A and 4B. The FIG. 4A graph represents the interrogation of lung tissue; whereas, the FIG. 4B graph represents the interrogation of heart tissue. Lung and heart tissue look more different in pulse inversion imaging that in conventional imaging. For example, lung tissue responded better to lower frequencies.

The FIG. 4A graph resulted from linear response of the lung tissue to self-demodulated signals. With wideband transmission, after nonlinear propagation the summation of the positive and the negative pulse will present a finite signal around 1 MHz, roughly half of the center frequency on transmit, a phenomenon called self-demodulation. Lung tissue responds to this low-frequency signal better than heart tissue. On the other hand, compared to lung tissue, heart tissue tends to favor higher frequency components in a PI mode because its stronger motion results in less perfect cancellation at higher frequencies.

Part of the algorithm involves estimating the center frequency of the RF data. Let r(n) be a sampled A-line signal and R(n) be its complex envelope. $f_c(n)$, the local center frequency of r(n), is related to R(n) by $$\arg\{R(n+1)R^*(n)\} \cong \frac{\arg\{R(n+1)R^*(n-1)\}}{2} \cong \frac{2\pi f_c(n)}{f_s}, \quad (1)$$

where $\arg\{\cdot\}$ denotes phase/argument and A is the sampling rate. Estimators of $f_c(n)$ can be derived based on (1). An example of an estimator is:

$$\hat{f}_c(n) \equiv \frac{\arg\left\{\sum_{i=-m}^{i=m} w(i)R(n+i+1)R^*(n+i-1)\right\}}{4\pi} f_s \quad (2)$$

as the estimator. Averaging based on the window function w(i) reduces variance.

In one example, transmitting is at 2.1 MHz in a high resolution mode, the sampling rate is 32 MHz and the beam density is 0.72 beam/degree. One image or frame consists of 64 beams with 2 transmits per beam. The RF echoes in a frame are denoted as $\{r_p(n, \theta), r_n(n, \theta)\}$, where the subscripts p and n stand for positive and negative pulse on transmit respectively, and n and $\theta=\theta(k)$ (k is the beam index) denote time index and angle respectively.

Figure 4C:
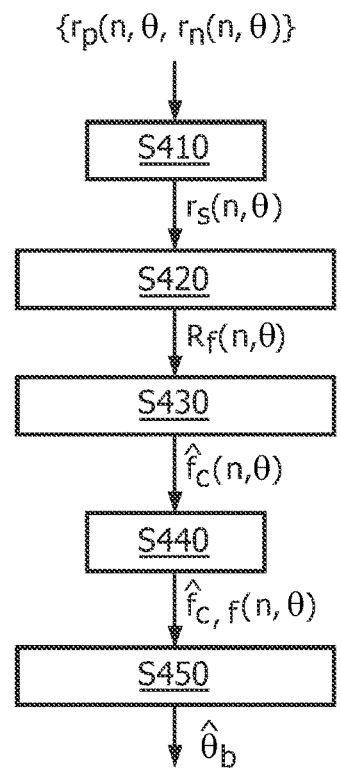

FIG. 4C shows the flow diagram of first version of the algorithm, where $r_s(n, \theta) = r_p(n, \theta) + r_n(n, \theta)$, $R_f(n, \theta) = r_s(n, \theta) \otimes h(n)$, $\otimes$ denotes convolution, and $h(n)$ is a 121-tap single-sided complex bandpass filter between 0.95 and 2.05 MHz. The center frequency map $\hat{f}_c(n, \theta)$, shown in FIG. 4D and discussed herein below, is obtained beam by beam based on equation (2) with a 301-tap Hamming window, and then smoothed by a 301 (axially or in the n direction) by 5 (laterally or in the $\theta$ direction) boxcar filter to get $\hat{f}_{c,f}(n, \theta)$. The last step is to estimate the boundary angle between heart and lung using the smoothed center frequency map $\hat{f}_{c,f}(n, \theta)$. The steps in FIG. 4C are summation (step S410), complex temporal filtering (step S420), center frequency estimation (step S430), 2D filtering (step S440) and boundary estimation (step S450).

Figure 4D:
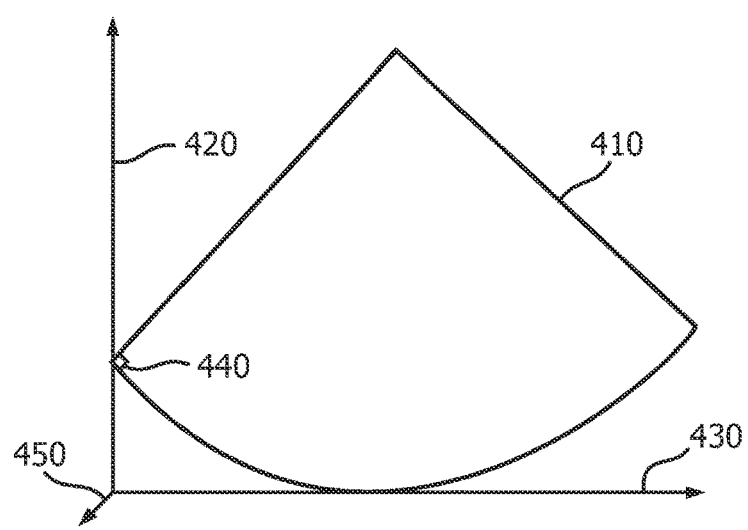

A center frequency map 410, corresponding to either $\hat{f}_c(n, \theta)$ or $\hat{f}_{c,f}(n, \theta)$, is illustrated in FIG. 4D along with an imaging depth axis 420 and a lateral axis 430. The map 410 spatially corresponds to the field of view 314 of FIG. 3. Point by internal point, it can be colored according to a spectrum indicative of respective center frequencies by voxel. The coloring visually indicates a spatial distinction between lung and heart tissue. The map 410 can be shown to users in place of the FIG. 3 presentation, or overlaid on a B-mode image, without even the need for extracting a spatial boundary. Or it can be shown alongside, and optionally concurrently with, the FIG. 3 presentation. A voxel or sub-volume 440 is definable within the imaging plane of the map 410 and extends along the depth and lateral axes 420, 430 and along an axial-directed axis 450, normal to the sheet of FIG. 4D. The center frequency map 410 spatially represents, for its imaging plane, the estimated center frequencies sub-volume by sub-volume for user visualization in distinguishing between heart and lung tissue. Optionally, the FIG. 3 presentation can be shown to users without displaying the center frequency map 410.

Estimation of the boundary angle involves multiple thresholding. Starting with the first thresholding relation: For a beam (i.e., give a $\theta$) to qualify as a heart region, the center frequency has to satisfy the following condition:

$$\frac{1}{1501}\sum_{m=0}^{1500} \hat{f}_{c,f}(n+m, \theta) \geq f_{u1} \text{ for all } n \in [1500, 2500]. \quad (3)$$

That is, only if the average center frequencies between the 1500th and 3000th points (between 36 mm and 72 mm), between the 1501st and 3001st points, . . . , and between the 2500th and 4000th points (between 60 mm and 96 mm) are all no lower than $f_{u1}$, can a beam be considered to be passing through heart tissue. The collection of the index of qualified beams is denoted as the set $A_1$. For example, $A_1=\{3, 4, \ldots, 28\}$ (noting that the 64 beams are counted from right to left in FIG. 3 and that the first two and last two beams do not qualify because of the spatial smoothing filter) for $f_{u1}=1.37$ MHz. Accordingly, the boundary angle can be estimated as the average angle over beams 28 and 29, $\theta(k)$ being an increasing function of k. The blockage boundary line 332 corresponds to the boundary angle.

The lung tissue can never appear on the right side of the heart (from the perspective patient) as long as the probe is correctly positioned, unless the image shown in FIG. 3 is, in effect, flipped. In other words, FIG. 3 shows a cross-sectional view from the arbitrarily-chosen perspective of looking from the head to the toes of a patient. The opposite perspective can instead be chosen, i.e., from the toes to the head. Based on the perspective shown in FIG. 3, we can therefore always estimate the boundary based on the leftmost beam satisfying the condition defined in (3). For example, if $A_1=\{14, 15, \ldots, 28\}$, the boundary angle still could be estimated as the average angle over beams 28 and 29. To navigate towards an apical view of the heart, FIG. 3 suggests movement of the probe toward the chest portion between the left and right ribcage.

Figure 5:
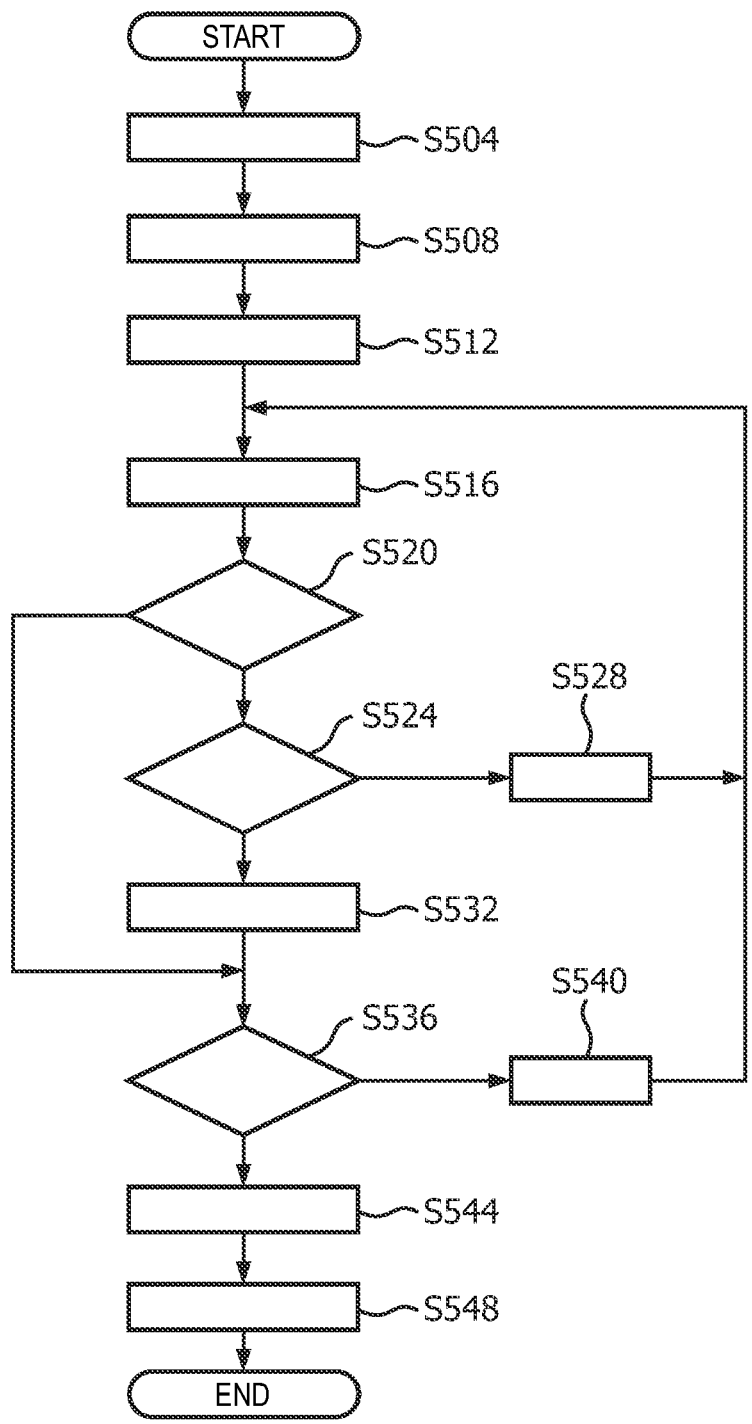
FIG. 5 is a flow chart on how center frequencies at various depths within a current field of view are utilized to set a spatial boundary between heart and lung tissue.

FIG. 5 summarizes the above example of a receive-center-frequency-based spatial boundary determination procedure 500. An estimate can initially be made of the center frequencies for all receive beams or "A-lines." This is done for all incremental imaging depths along an A-line. Specifically a pulse and the following identical or inverted pulse are issued ray line by ray line to generate, for each ray line, one or more A-lines that are separately sampled for respective incremental imaging depths (step S504). The current candidate beam is initialized to beam 3. The first two beams are skipped due to spatial smoothing, as mentioned above (step S508). The current window is initialized to the 1500th and 3000th points (or "sampling locations") of respective imaging depth (step S512). 1501 points is the window length. The average of the center frequencies for the locations in the current window is computed (step S516). If the average equals or exceeds the $f_{u1}$ threshold, as shown above in formula (3) (step S520), query is made as to whether beam screening for qualification is complete (step S524). If it is not complete (step S524), the window is slid forward by one sampling location (step S528). If, on the other hand, screening is complete (step S524), the current candidate beam is now deemed to be qualified (step S532). Also, if the center frequency average is less than the the $f_{u1}$ threshold (step S520), the qualification step S532 is skipped, and the current beam is not qualified. In either event, qualification or not, if a next receive beam exists (step S536), that next beam serves as the current beam (step S540) in a branch back to average computation step S516. If, instead a next beam no longer exists (step S536), the leftmost beam from among those qualified is selected (step S544). The spatial boundary, for the current imaging plane, is set for in between the selected beam and its neighboring beam on the left (step S548).

Robustness of lung identification can be improved by including additional criteria. The second threshold is used to detect regions with very low center frequency: Given a beam angle $\theta$, if the center frequency satisfies $$\frac{1}{501}\sum_{m=0}^{500} \hat{f}_{c,f}(n+m, \theta) < f_1 \text{ for any } n \in [1750, 3750], \quad (4)$$

this beam can be considered passing through lung tissue. The collection of the indices of beams satisfying (4) is denoted as $A_2$. $A_2=\{36, 37, \ldots, 62\}$ in the case shown in Figure 3 for $f_1=1.27$ MHz and therefore has no conflict with the corresponding $A_1$.

The third (and the last) threshold is used to detect regions with very high center frequency: Given a beam angle $\theta(k)$, if the center frequency satisfies $$\frac{1}{2001}\sum_{n=2000}^{4000} \hat{f}_{c,f}[n, \theta(k+m)] > f_{u2} \text{ for all } m \in \{-2, -1, 0, 1, 2\}, \quad (5)$$

this beam is considered to be passing through heart tissue. That is, if 5 consecutive beams present very high center frequency, the central beam has a high chance of passing heart tissue. The collection of the index of beams satisfying (5) is denoted as $A_3$.

In practice, $A_1$, $A_2$ and $A_3$ might not be consistent with each other. For example, the intersection of $A_1$ and $A_2$ might be nonempty meaning that some beam could be considered passing both heart and lung tissue. Accordingly, the collections may be prioritized. Specifically $A_3$ (the very high frequency condition defined in (5)) is given the highest priority and $A_1$ (the high frequency condition defined in (3)) is given the lowest priority. The "adjusted heart tissue set" is defined as $$A_h \equiv \{k | k \in A_1 \text{ and } k < l \text{ for any } l \in A_2 \text{ that is larger than } \max(A_3)\}, \quad (6)$$

where $\max(A_3)$ is the maximum element of $A_3$ and is defined as $-\infty$ if $A_3$ is empty. The following is an equivalent definition:

$$A_h \equiv \{k | k \in A_1 \text{ and } k < l \text{ for any } l \in A_2'\} \quad (7)$$

where $$A_2' \equiv \{l | l \in A_2 \text{ and } l > j \text{ for any } j \in A_3\}. \quad (8)$$

The boundary between heart and lung is estimated based on the largest element of $A_h$. For example, if $A_1 = \{5, 6, \ldots, 50\}$, $A_2 = \{3, 4, 49, 50, 51\}$ and $A_3 = \{11, 12, 13\}$, then $A_2' = \{49, 50, 51\}$, $A_h = \{5, 6, \ldots, 48\}$, and the estimated boundary angle $\theta_b$ is the average angle over beams 48 and 49. An empty $A_h$ indicates lung tissue occupying the whole image. If $A_h$ is not empty, $$\hat{\theta}_b \equiv \frac{1}{2}\{\theta[\max(A_h)] + \theta[\max(A_h) + 1]\} = \theta[\max(A_h)] + \frac{1}{2}\Delta\theta, \quad (9)$$

where $\Delta\theta = \theta(k+1) - \theta(k)$. Because the 2D smoothing filter deteriorates beams on the sides, it is concluded that no lung tissue appears in the image if $$= 64 - \frac{5-1}{2} = 62.$$

The role of $f_{u1}$ is much more important than that of but occasionally existence of $A_2$ contributes positively in determining the boundary. To recap, in this first version of the algorithm, $f_{u1} = 1.37$ MHz, $f_1 = 1.27$ MHz, and $f_{u2} = \infty$.

Figure 6:
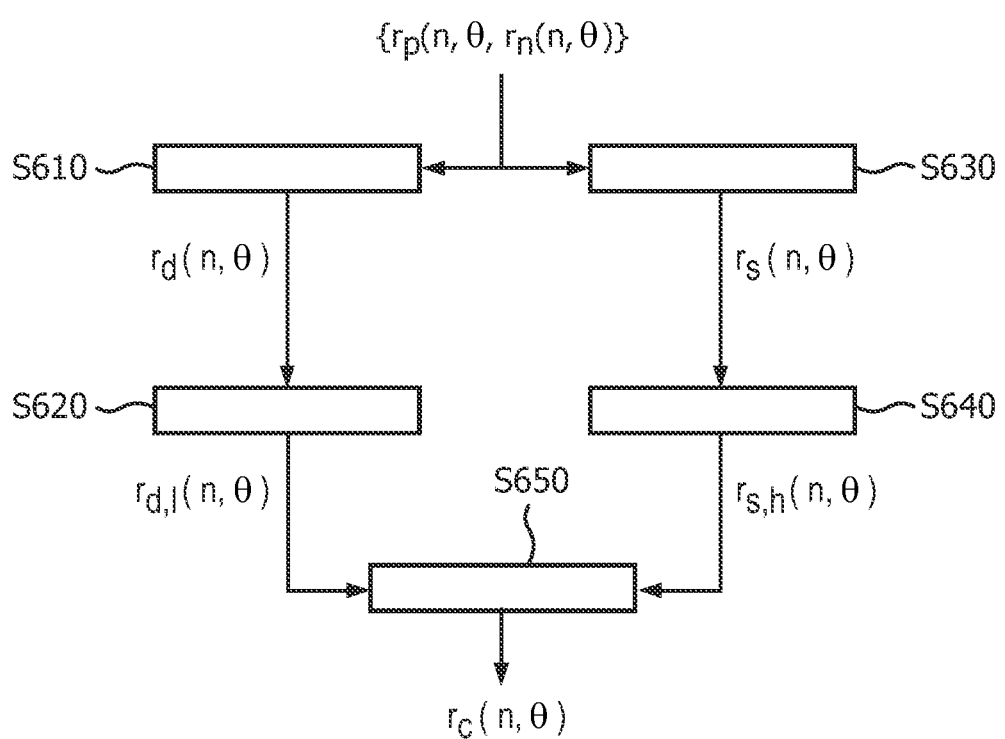
FIG. 6 is a flow chart representative of an exemplary lung identification algorithm based on a one-dimensional probe.

A second version of the algorithm also pertains to 1D probes and for PI data acquired in high resolution mode. As mentioned above, lung tissue responds to low-frequency signal components well in a linear fashion and motion causes less perfect cancellation at higher frequencies in heart tissue in a PI mode. This implies the possibility of performance improvement by replacing $r_s(n, \theta)$ with a composite signal $r_c(n, \theta)$ in the signal processing chain shown in FIG. 4C. For this reason, there is a second version of the algorithm. FIG. 6 shows how $r_c(n, \theta)$ is formed, where $$r_d(n,\theta) \equiv r_p(n,\theta) - r_n(n,\theta) \text{ which is step } S610,$$

$$r_{d,l}(n,\theta) \equiv r_d(n,\theta) \otimes h_l(n) \text{ which is step } S620,$$

step S630 is identical to step S410, $r_{s,h}(n, \theta) \equiv r_s(n, \theta) \otimes h_h(n)$ which is step S640, $r_c(n, \theta) \equiv w_d r_{d,l}(n, \theta) + w_s r_{s,h}(n, \theta)$ which is step S650, $h_l(n)$ is a 101-tap real lowpass filter cutting off at 0.8 MHz, and $h_h(n)$ is a 101-tap real highpass filter cutting off at 1.15 MHz. Echoes from lung tissue favor $r_{d,l}(n, \theta)$ (because it responds to low-frequency components well) and echoes from heart tissue favor $r_{s,h}(n, \theta)$ (because of more motion). $w_d$ and $w_s$ are weights used to balance the two forces. The signal processing following $r_c(n, \theta)$ remains the same as that following $r_s(n, \theta)$ in FIG. 4C. Exemplary parameters are $w_d = 1.2$, $w_s = 1$, $f_{u1} = 1.4$ MHz, $f_1 = 1.2$ MHz, and $f_{u2} = 1.5$ MHz. It is within the intended scope of the invention to use one or more of the thresholds $f_{u1}$, $f_1$ and $f_{u2}$ and correspondingly one or more of $A_1$, $A_2$ and $A_3$.

A matrix probe version of the algorithm is based on the second version—composite signals are used for center frequency estimation. RF data can be collected, for example, using penetration imaging mode with PI enabled and a center frequency of 2.2 MHz. Lateral and elevational widths can be maximal.

Each volume has 40 (lateral) by 33 (elevational) A-lines (with 2 transmit events per A-line due to PI acquisition). That is, RF echoes $\{r_p(n, \theta, \phi), r_n(n, \theta, \phi)\}$ with 40 $\theta$ values and 33 $\phi$ values are obtained. The lateral beam density is 0.41 beam per degree.

Figure 7:
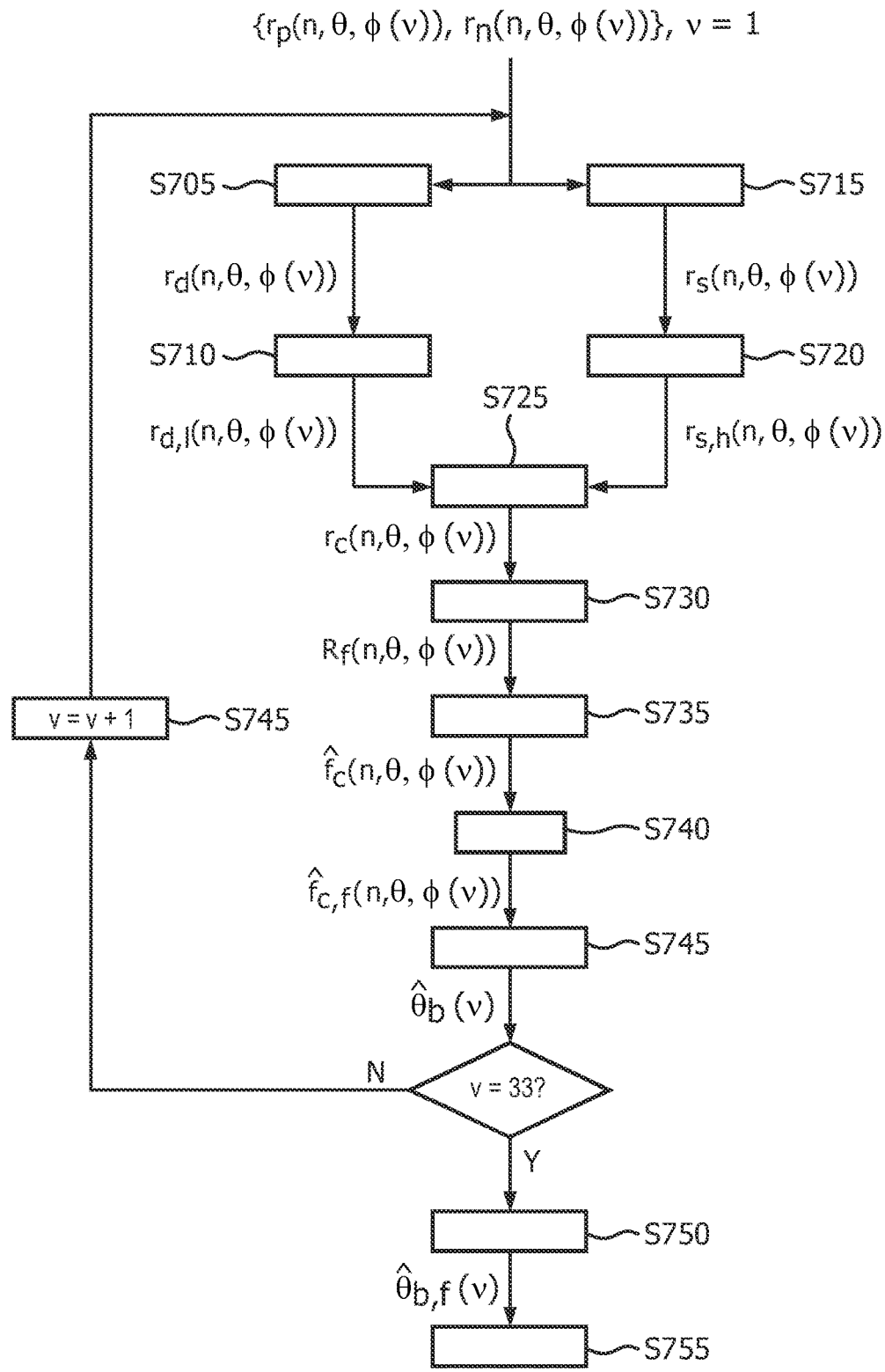
FIG. 7 is a flow chart representative of an exemplary lung identification algorithm based on a matrix probe.

FIG. 7 shows the flow diagram of the matrix probe version of the algorithm, with the temporal sampling rate at 16 MHz. The steps are: subtraction (step S705), low-pass filtering (step S710), summation (step S715), high-pass filtering (step S720), weighted summation (step S725), complex temporal filtering (step S730), center frequency estimation (step S735), 2D filtering (step S740), boundary estimation (step S745), median filtering (step S750) and visualization across planes (step S755). In short, $\phi = \phi(v)$, $r_d(n, \theta, \phi) \equiv r_p(n, \theta, \phi) - r_n(n, \theta, \phi)$, $r_s(n, \theta, \phi) \equiv r_p(n, \theta, \phi) + r_n(n, \theta, \phi)$, $r_{d,l}(n, \theta, \phi) \equiv r_d(n, \theta, \phi) \otimes h_l(n)$, $r_{s,h}(n, \theta, \phi) \equiv r_s(n, \theta, \phi) \otimes h_h(n)$, $r_c(n, \theta, \phi) \equiv w_d r_{d,l}(n, \theta, \phi) + w_s r_{s,h}(n, \theta, \phi)$, $h_l(n)$ is a 51-tap real lowpass filter cutting off at 0.8 MHz, $h_u(n)$ is a 51-tap real highpass filter cutting off at 1.3 MHz, $w_d = 2$, and $w_s = 1$. The complex envelope $R_c(n, \theta, \phi) \equiv r_c(n, \theta, \phi) \otimes h(n)$, where $h(n)$ is a 61-tap single-sided complex bandpass filter between 0.95 and 2.05 MHz. In each elevational plane, the center frequency map $\hat{f}_c(n, \theta, \phi)$ is obtained beam by beam based on equation (2) with a 151-tap Hamming window, and then smoothed by a 151 (in the n direction) by 3 (in the $\theta$ direction) boxcar filter to get $\hat{f}_{c,f}(n, \theta, \phi)$.

For boundary estimation, the following are defined:

$$A_{1,v} \equiv \left\{k \left| \frac{1}{751} \sum_{m=0}^{750} \hat{f}_{c,f}(n+m, \theta(k), \phi(v)) \geq f_{u1} \text{ for all } n \in [750, 1250] \right.\right\}. \quad (10)$$

$$A_{2,v} \equiv \left\{k \left| \frac{1}{251} \sum_{m=0}^{250} \hat{f}_{c,f}(n+m, \theta(k), \phi(v)) < f_{u1} \text{ for all } n \in [875, 1875] \right.\right\}, \quad (11)$$

and $$A_{3,v} \equiv \left\{k \left| \frac{1}{1001} \sum_{n=1000}^{2000} \hat{f}_{c,f}(n, \theta(k+m), \phi(v)) \geq f_{u2} \text{ for all } m \in \{-1, 0, 1\} \right.\right\}, \quad (12)$$

where, illustratively $f_{u1} = 1.38$ MHz and is the only threshold used. Equivalently $f_1 \equiv 0$, $f_{u2} \equiv \infty$, $A_{2,v}$ and $A_{3,v}$ are empty, and the adjusted heart tissue set $A_{h,v} = A_{1,v}$.

The boundary angle between heart and lung in the v-th plane is $$\hat{\theta}_b(v) \equiv \begin{cases} \theta(1) - \frac{1}{2}\Delta\theta & \text{if } A_{h,v} \text{ is empty} \\ \theta(40) + \frac{1}{2}\Delta\theta & \text{if } \max(A_{h,v}) \geq 40 - \frac{3-1}{2} = 39 \\ \theta[\max(A_{h,v})] + \frac{1}{2}\Delta\theta & \text{otherwise} \end{cases} \quad (13)$$

A 5-tap median filter (a function of v) in the elevational direction is then applied to $\hat{\theta}_b(v)$ and the output is denoted as $\hat{\theta}_{b,f}(v)$. From the filtered boundary angles $\hat{\theta}_{b,f}(v)$, a map indicating heart region can be derived to provide cross-plane visualization. To remove outliers around the boundary between heart and lung which appear occasionally, only the largest connected region is displayed. The clinician can use the cross-plane visualization map or the FIG. 3 display to interactively manipulate the probe 116 so as to avoid the lung, in, for example, navigating the probe to acquire a standard view of the heart.

Figure 8:
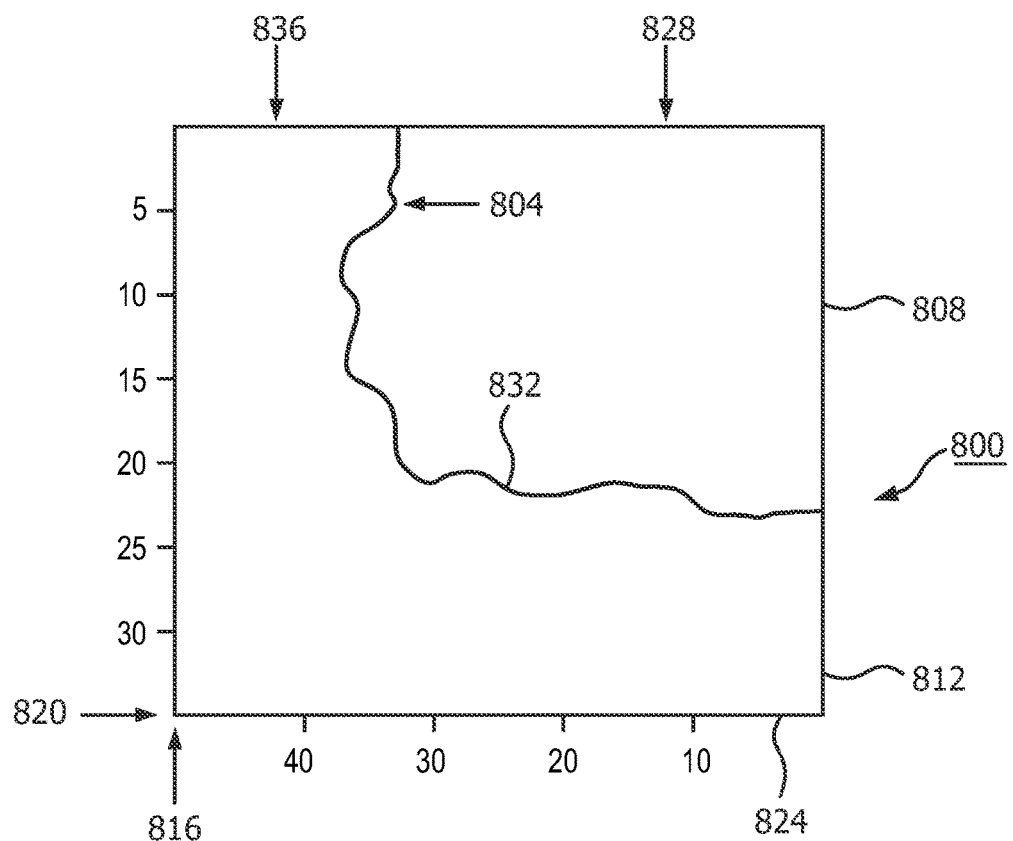
FIG. 8 is an on-screen guidance image that multi-dimensionally depicts a three-dimensional path of a boundary between heart tissue and lung tissue that are within the current field of view of the imaging probe.

FIG. 8 is cross-plane visualization map 800, having a beam index on the horizontal axis and a plane index on the vertical axis. It serves as an on-screen guidance image that multi-dimensionally depicts a three-dimensional path 804 of a boundary between heart tissue 808 and lung tissue 812 that are within the current field of view 214 of the imaging probe 116. Here, the probe is a matrix probe with electronic steering so that, with the probe in a given positioning, boundaries 332 are calculated for incremental imaging planes v, the increments being in an elevational direction 816. In the onscreen depiction, lateral and elevational components 820, 816 of the path 804 jointly vary along the path. The lateral axis represents candidate A-lines 824; whereas, the vertical axis represents imaging planes. A heart region 828 above and to the right of a multi-dimensional, i.e., lateral and elevational, depiction 832 of the path 804 may be colored distinctively, such as red. A lung region 836 to the left and below can be colored blue, for example. Alternatively, FIG. 3 can be reoriented, as suggested above, so as to assume the toe to head perspective, so that the green arrow 336 is pointing rightward instead of leftward; likewise, the heart region 828 in FIG. 8 would be positioned to the left with the lung region 836 to the right.

To navigate towards an apical view of the heart, FIG. 8 suggests movement of the probe both toward the chest portion between the left and right ribcage and toward the head.

Alongside the cross-plane visualization map 800, an ultrasound image such as that shown in FIG. 3 can present an imaging plane in the axial direction. The maps, the ultrasound images and the graphics optionally can be selectively invoked, placed and adjusted by the clinician, via the user controls 132 such as a keyboard, to arrange the overall, dynamically updated, interactive graphical user interface (GUI).

Lung identification can, as mentioned above, alternatively be performed without pulse inversion. The following discussion is based on 2D images (1D probes) for simplicity. The concept applies to both 1D and matrix probes.

Recall that the composite signal $$r_c(n,\theta) = w_d \cdot [r_p(n,\theta) - r_n(n,\theta)] \otimes h_l(n) + w_s \cdot [r_p(n,\theta) + r_n(n,\theta)] \otimes h_n(n), \quad (14)$$

where $r_p(n, \theta)$ and $r_n(n, \theta)$ are interleaved, meaning that the temporal acquisition sequence is $\langle r_p(n, \theta(1)), r_n(n, \theta(1)),$ $r_p(n, \theta(2)), r_n(n, \theta(2)), \ldots \rangle$. Since the power in $[r_p(n, \theta) + r_n(n, \theta)]$ within the passband of $h_h(n) \otimes h(n)$ is dominated by motion of heart tissue, $[r_p(n, \theta) + r_n(n, \theta)] \otimes h_h(n) \otimes h(n)$ can be approximated by $[r_p(n, \theta) - r_{p2}(n, \theta)] \otimes h_h(n) \otimes h(n)$, where $\{r_{p2}(n, \theta)\}$ is obtained by replacing the negative pulses on transmit for getting $\{r_n(n, \theta)\}$ by positive pulses (that is, the new acquisition sequence is $\langle r_p(n, \theta(1)), r_{p2}(n, \theta(1)), r_p(n, \theta(2)), r_{p2}(n, \theta(2)), \ldots \rangle$). In addition, $r_p(n, \theta) - r_n(n, \theta) \equiv r_p(n, \theta) + r_{p2}(n, \theta)$. Accordingly, $$r_c'(n,\theta) \otimes h(n) \cong r_c(n,\theta) \otimes h(n), \quad (15)$$

where $$r_c'(n,\theta) \equiv w_d \cdot [r_p(n,\theta) + r_{p2}(n,\theta)] \otimes h_l(n) + w_s \cdot [r_p(n,\theta) - r_{p2}(n,\theta)] \otimes h_h(n). \quad (16)$$

Implied by (15) is that lung tissue can be detected against heart using only positive (or only negative) pulses on transmit. One benefit from this is no worry of mismatch between the positive and the negative pulse. Alternatively, such a scheme can be employed jointly or interleavingly with pulse inversion.

Issuance of ultrasound pulses to a volume and receiving echo data is followed by estimating, based on the received data, center frequency subvolume-by-subvolume. Distinguishing between heart and lung tissue occurs based on a result of the estimating, and may include automatically identifying a spatial boundary between the heart and lung tissue, or a user display of center frequencies that allows for visual distinguishing. The issuance can include issuing, ray line by ray line, pair-wise identical, and/or pair-wise mutually inverted, ultrasound pulses. Center frequency calculations may be made for incremental sampling locations of respective imaging depth along each of the A-lines generated from echo data of the rays. The distinguishing might entail averaging center frequencies for locations along an A-line, and applying a central frequency threshold to the average. The leftmost of the qualifying A-lines, i.e., that meet the threshold, may determine the spatial boundary in the current imaging plane.

In addition to making diagnostic cardiac examination performable by nurses or other clinicians who may be untrained specifically in sonography, the apparatus 100 can guide novice sonographers. The apparatus 100 can feature, for this purpose or this mode, a regular (grayscale) sonogram, along with the visual feedback described herein above. Alternatively, the novel visual feedback of the apparatus 100 can speed up the work flow of trained or experienced sonographers.

While the invention has been illustrated and described in detail in the drawings and foregoing description, such illustration and description are to be considered illustrative or exemplary and not restrictive; the invention is not limited to the disclosed embodiments.

For example, instead of a green arrow on the display pointing to the lung tissue side of the boundary, short hash marks can appear attached to the boundary but on the side of the lung tissue.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus comprising:
    an ultrasound interface module configured for issuing ultrasound pulses to a volume and for receiving echo data; and
    a center frequency determination module configured to estimate a center frequency of the received echo data at each of a plurality of locations in the volume; and
    a tissue discrimination module configured, for each of the plurality of locations, to assign a given location as corresponding to lung tissue, heart tissue, or a spatial boundary between said heart and lung tissue based upon a determination that the estimated center frequency for the given location is higher or lower than, respectively, a given threshold.

2. The apparatus of claim 1, further comprising a matrix probe, said boundary having a three-dimensional path, said apparatus further comprising a display, said apparatus configured for displaying, via said display, said path multi-dimensionally for a given position of said probe.

3. The apparatus of claim 2, said displaying using a representation that shows how lateral and elevational components of said path jointly vary along said path.

4. The apparatus of claim 1, further comprising:
    a display; and
    an ultrasound imaging probe for said issuing and said receiving,
    said apparatus configured for presenting, via said display, the identified boundary to provide user guidance, while imaging, for moving said probe to achieve a target view.

5. The apparatus of claim 1, wherein the identification of the spatial boundary comprises selecting from among A-lines based on the threshold.

6. The apparatus of claim 5, said selecting comprising applying the threshold at each of the plurality of locations along a given one of said A-lines.

7. The apparatus of claim 5, wherein the identification of the spatial boundary comprises qualifying candidate A-lines for the selecting, the selected A-line defining the spatial boundary between said heart and lung tissue.

8. The apparatus of claim 7, said qualifying of a candidate A-line relying on center frequency data of said candidate A-line to the exclusion of center frequency data of the other candidate A-lines.

9. The apparatus of claim 1, said identification of the spatial boundary comprising averaging center frequencies for locations along an A-line, and applying a central frequency threshold to the average.

10. The apparatus of claim 9, configured for iteratively performing said averaging, and respectively said applying, in correspondence with different positions along said A-line.

11. The apparatus of claim 1, said issuing comprising issuing, ray line by ray line, pair-wise identical, and/or pair-wise mutually inverted, ultrasound pulses.

12. The apparatus of claim 11, said ultrasound module configured for, in case of issuing pair-wise identical pulses, computing a difference between an echo of one of the pair and an echo of the other of the pair.

13. The apparatus of claim 11, said ultrasound module configured for, in case of inverted pulses, ultrasound pulse inversion by which an inverted copy of a just preceding pulse is issued and summing an echo of said copy with an echo of said just preceding pulse.

14. The apparatus of claim 1, said estimating being performed at each of the plurality of locations along a given A-line.

15. The apparatus of claim 1, configured for subjecting data derived from said receiving to low pass filtering.

16. The apparatus of claim 15, configured for subjecting data derived from said receiving to high pass filtering.

17. The apparatus of claim 16, configured for combining, for said estimating, the low pass filtered data with the high pass filtered data.

18. The apparatus of claim 17, said combining comprising assigning a first weight to the low pass filtered data, assigning a second weight to the high pass filtered data, and computing a weighted average that uses the weights.

19. The apparatus of claim 15, said receiving comprising receiving pulse inversion samples, said estimating comprising computing a difference between, and a sum of, a pair of said samples and performing said low pass filtering on the difference and said high pass filtering on the sum.

20. The apparatus of claim 15, said deriving comprising computing:
    in case of pulse inversion, a difference between an echo from a pulse, from among said pulses, and an echo from an inversion of said pulse, to yield said data derived; and,
    in case of pulse subtraction, a sum of respective echoes of said pulse and a pulse identical to said pulse, to yield said data derived.

21. The apparatus of claim 1, further comprising a display and configured for displaying, on said display, a center frequency map that, for an imaging plane, spatially represents the estimated center frequencies at each of the plurality of locations.

22. The apparatus of claim 1, wherein the tissue discrimination module is configured to determine a spatially selected region of the volume and assign each of the plurality of given locations within the spatially selected region as corresponding to either lung tissue or heart tissue based upon the determination that the estimated center frequency for the given location is higher or lower than a given threshold.

23. A computer readable medium embodying a computer program for body tissue discrimination, said program having instructions executable by a processor to perform a plurality of acts, such that from among said plurality are the acts of:
    issuing ultrasound pulses to a volume and for receiving echo data; and
    estimating, based on the received data, a center frequency of the received echo data at each of a plurality of locations in the volume; and
    determining, for each of the plurality of locations, that a given location corresponds to lung tissue, heart tissue, or a spatial boundary between said heart and lung tissue based on a determination that the estimated center frequency for the given location is higher or lower than a given threshold.

\* \* \* \* \*